US011996191B2

(12) United States Patent
Stahl et al.

(10) Patent No.: US 11,996,191 B2
(45) Date of Patent: May 28, 2024

(54) SYSTEMS AND METHODS FOR DEVICE CONTROL

(71) Applicant: SHANGHAI UNITED IMAGING HEALTHCARE CO., LTD., Shanghai (CN)

(72) Inventors: Johannes Stahl, Houston, TX (US); Walter Aguilar, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 319 days.

(21) Appl. No.: 17/033,967

(22) Filed: Sep. 28, 2020

(65) Prior Publication Data

US 2021/0012893 A1 Jan. 14, 2021

(51) Int. Cl.
*G16H 40/67* (2018.01)
*H04L 9/08* (2006.01)
*H04L 9/30* (2006.01)

(52) U.S. Cl.
CPC ............. *G16H 40/67* (2018.01); *H04L 9/088* (2013.01); *H04L 9/30* (2013.01)

(58) Field of Classification Search
USPC .......................................................... 705/2
See application file for complete search history.

(56) References Cited

U.S. PATENT DOCUMENTS

| 9,871,772 B1 | 1/2018 | Weinstein et al. |
| 10,304,322 B2 | 5/2019 | Bossier et al. |

(Continued)

FOREIGN PATENT DOCUMENTS

| CN | 110827969 A | 2/2020 |
| CN | 111654503 A | 9/2020 |

(Continued)

OTHER PUBLICATIONS

Zhang, M. (2013). Energy-efficient designs for securing embedded and mobile computing systems (Order No. 3562172). Available from ProQuest Dissertations and Theses Professional. (1367601949). Retrieved from https://dialog.proquest.com/professional/ docview/ 1367601949?accountid=131444 (Year: 2013).*

(Continued)

*Primary Examiner* — Christopher L Gilligan
*Assistant Examiner* — Bennett Stephen Erickson
(74) *Attorney, Agent, or Firm* — METIS IP LLC

(57) ABSTRACT

A system includes a remote control device configured to remotely control a device and a safety control device communicating with each other via a wireless connection. The remote control device includes a switch, a motion enable unit configured to generate processed information by processing information using a first secret, and a hand control unit capable of acquiring the processed information only when the switch is in a closed state and configured to transmit the processed information to the safety control device via the wireless connection. The safety control device includes a communication unit configured to receive the processed information via the wireless connection and a safety control unit configured to verify the closed state of the switch by processing the processed information using a second secret that matches the first secret and enable control of the device when the closed state of the switch is verified.

19 Claims, 8 Drawing Sheets

(56) References Cited

U.S. PATENT DOCUMENTS

| | | | |
|---|---|---|---|
| 11,651,379 B1* | 5/2023 | Asefi | G06Q 30/02 |
| | | | 705/65 |
| 2005/0203582 A1 | 9/2005 | Healy et al. | |
| 2011/0228936 A1 | 9/2011 | Silvermint | |
| 2014/0044265 A1* | 2/2014 | Kocher | G06F 21/71 |
| | | | 380/277 |
| 2014/0074493 A1* | 3/2014 | Schneider | G16H 15/00 |
| | | | 340/5.82 |
| 2015/0207626 A1 | 7/2015 | Neftel et al. | |
| 2017/0237565 A1 | 8/2017 | Rommel | |
| 2017/0308665 A1 | 10/2017 | Heck et al. | |
| 2018/0264347 A1* | 9/2018 | Tran | A63B 69/38 |
| 2018/0375839 A1 | 12/2018 | Dattolo et al. | |
| 2020/0169414 A1 | 5/2020 | Ekdahl et al. | |
| 2021/0359843 A1* | 11/2021 | Li | H04L 63/065 |
| 2022/0188443 A1* | 6/2022 | Shaw | G06F 21/602 |
| 2022/0191700 A1* | 6/2022 | Jung | H04L 9/3242 |
| 2022/0247555 A1* | 8/2022 | Gullberg | H04W 12/37 |

FOREIGN PATENT DOCUMENTS

| | | |
|---|---|---|
| EP | 3605989 B1 | 10/2020 |
| WO | 2019103913 A1 | 5/2019 |

OTHER PUBLICATIONS

Zheng, Yan et al., Constrains of Key Management in Wireless Sensor Network, Computer Technology and Development, 16(10): 118-121& 170, 2006.

Taketsugu Yao et al., Initial Common Secret Key Sharing using Random Plaintexts for Short-range Wireless Communications, IEEE Transactions on Consumer Electronics, 55(4): 2025-2033, 2009.

* cited by examiner

SYSTEMS AND METHODS FOR DEVICE CONTROL

TECHNICAL HELD

The present disclosure generally relates to device control technology, and more particularly, to systems and methods for controlling a device via a remote control.

BACKGROUND

Medical devices are widely used in disease diagnosis and/or treatment. For example, a patient may be scanned by an imaging device to acquire image data of the patient for analysis, and/or treated by a treatment device. Before or during the scan or treatment of the patient, a user (e.g., a doctor, a nurse) may need to control the medical device via a control device.

SUMMARY

An aspect of the present disclosure relates to a system for controlling a device. The system may include a remote control device and a safety control device communicating with each other via a wireless connection. The remote control device may be configured to remotely control the device. The remote control device may include a switch, a motion enable unit, and a hand control unit. The motion enable unit may be configured to generate processed information by processing information using a first secret. The hand control unit may be capable of acquiring the processed information from the motion enable device only when the switch is in a closed state. The hand control unit may be configured to transmit the processed information to the safety control device via the wireless connection. The safety control device may include a communication unit and a safety control unit. The communication unit may be configured to receive the processed information via the wireless connection. The safety control unit may be configured to verify the closed state of the switch by processing the processed information using a second secret that matches the first secret. Further, the safety control unit may be configured to enable control of the device when the closed state of the switch is verified.

In some embodiments, the hand control unit and the motion enable unit may be connected to each other via a wired connection.

In some embodiments, the safety control unit may be configured to obtain a code. To generate the processed information, the motion enable unit may be configured to generate an encrypted code by encrypting the code using the first secret. To verify the closed state of the switch, the safety control unit may be configured to generate a decrypted code by decrypting the encrypted code using the second secret and compare the decrypted code with the code.

In some embodiments, the safety control unit may be configured to generate an encrypted code by encrypting a code using the second secret.

In some embodiments, to generate the processed information, the motion enable unit may be configured to generate a decrypted code by decrypting the encrypted code using the first secret. To verify the closed state of the switch, the safety control unit may be configured to compare the decrypted code with the code.

In some embodiments, the safety control unit may be configured to obtain a code. To generate the processed information, the motion enable unit may be configured to generate a first encrypted code by encrypting the code using the first secret. To verify the closed state of the switch, the safety control unit may be configured to generate a second encrypted code by encrypting the code using the second secret and compare the first encrypted code with the second encrypted code.

In some embodiments, the motion enable unit may be configured to obtain a first code. To generate the processed information, the motion enable unit may be configured to generate an encrypted code by encrypting the first code using the first secret. To verify the closed state of the switch, the safety control unit may be configured to obtain a second code, generate a decrypted code by decrypting the encrypted code using the second secret, and compare the decrypted code with the second code, wherein the first code and the second code have a same value.

In some embodiments, each of the first code and the second code may have a starting value.

In some embodiments, the first code may be generated by the motion enable unit according to an updating scheme, and the second code may be generated by the safety control unit according to the updating scheme.

In some embodiments, the updating scheme may include performing code updating at each of a series of time points.

In some embodiments, the updating may be performed based on a starting value using a timestamp generator or a pseudo-random number generator.

In some embodiments, the motion enable unit may be further configured to generate updated processed information by processing updated information using the first secret. The hand control unit may be further configured to transmit the updated processed information to the safety control device via the wireless connection. The communication unit may be further configured to receive the updated processed information via the wireless connection. The safety control unit may be further configured to verify the closed state of the switch by processing the updated processed information using the second secret and enable control of the device when the closed state of the switch is verified.

In some embodiments, the first secret and the second secret may be the same.

In some embodiments, the first secret may be a private key and the second secret may be a public key.

In some embodiments, the first secret may be the public key and the second secret may be the private key.

In some embodiments, the switch may be a physical key on the motion enable unit.

A further aspect of the present disclosure relates to a method for controlling a device. The method may be implemented on a remote control device and a safety control device communicating with each other via a wireless connection. The remote control device may be configured to remotely control the device. The remote control device may include a switch, a motion enable unit, and a hand control unit. The safety control device may include a communication unit and a safety control unit. The method may include generating, by the motion enable unit, processed information by processing information using a first secret; acquiring, by the hand control unit, the processed information from the motion enable device only when the switch is in a closed state; transmitting, by the hand control unit, the processed information to the safety control device via the wireless connection; receiving, by the communication unit, the processed information via the wireless connection; verifying, by the safety control unit, the closed state of the switch by processing the processed information using a second secret that matches the first secret; and enabling control of the device when the closed state of the switch is verified.

A still further aspect of the present disclosure relates to a non-transitory computer readable medium including executable instructions. The executable instructions may be executed by a remote control device and a safety control device communicating with each other via a wireless connection. The remote control device may be configured to remotely control the device. The remote control device may include a switch, a motion enable unit, and a hand control unit. The safety control device may include a communication unit and a safety control unit. When the executable instructions are executed by the remote control device and the safety control device, the executable instructions may direct the remote control device and the safety control device to perform a method. The method may include generating, by the motion enable unit, processed information by processing information using a first secret; acquiring, by the hand control unit, the processed information from the motion enable device only when the switch is in a closed state; transmitting, by the hand control unit, the processed information to the safety control device via the wireless connection; receiving, by the communication unit, the processed information via the wireless connection; verifying, by the safety control unit, the closed state of the switch by processing the processed information using a second secret that matches the first secret; and enabling control of the device when the closed state of the switch is verified.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
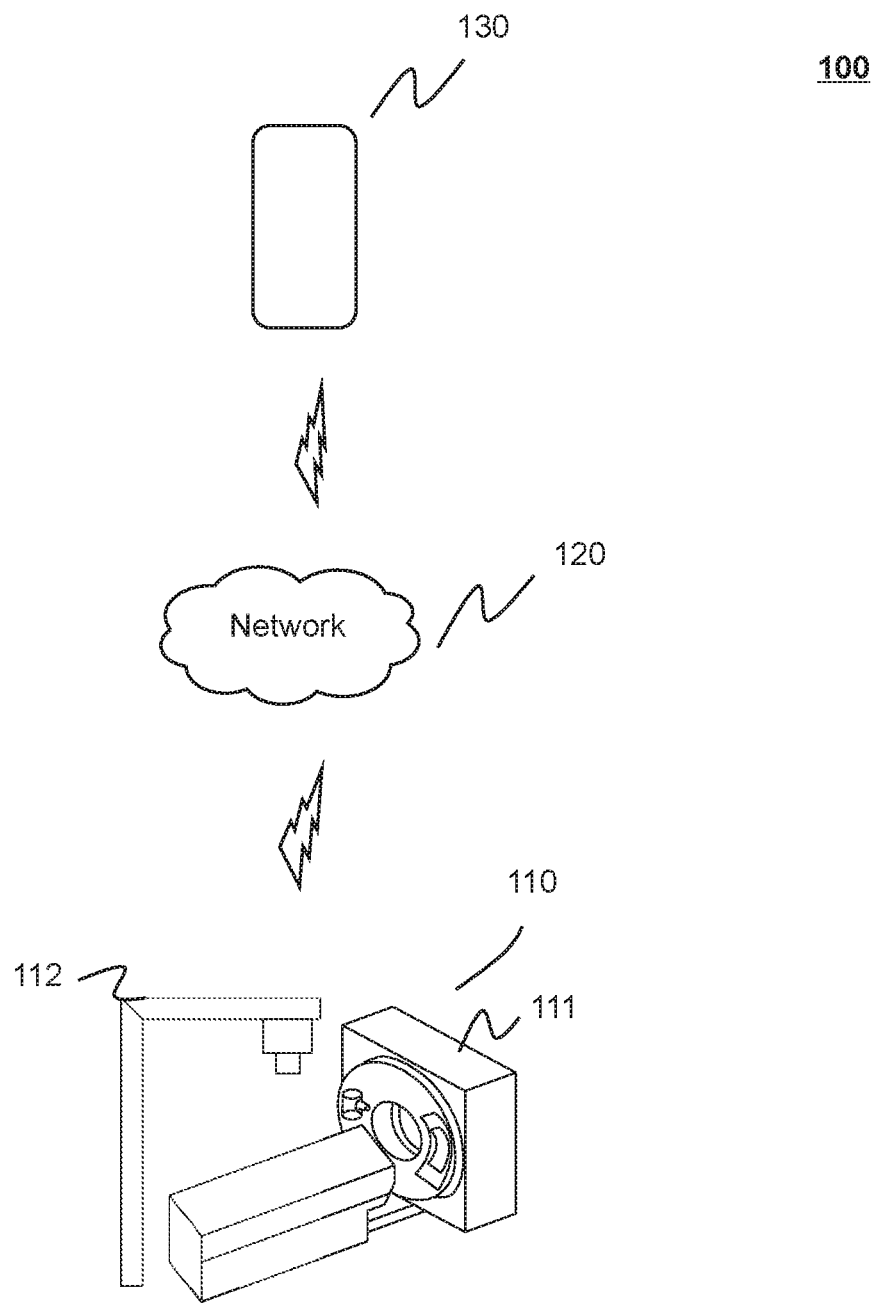
FIG. 1 is a schematic diagram illustrating an exemplary medical control system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms, "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," "or coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and components for non-invasive imaging and/or treatment, such as for disease diagnosis, treatment or research purposes. In some embodiments, the systems may include a radiotherapy (RT) system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

It is common that a device, or a portion thereof, e.g., a medical device or a component (e.g., a linear accelerator) of the medical device, is controlled by a control device that is connected to the device via a wired connection (e.g., a wire, a cable) to improve or ensure accurate control for safety or other considerations. However, such a hard-wired control device is inconvenient to use because the wire or cable may get in the way on the floor and the control device can only be used in a specific range constrained by the limited length of the wire or cable. Therefore, it is desirable to control the device via a remote control device (or referred to as a wireless control device) that is connected to the device via a wireless connection. However, wireless communication between the remote control device and the device often involves software which is not equivalent to hardware in terms of safety. For example, software errors or wireless transmission issues may occur and result in a false control instruction of the device or failure to transmit a valid and critical instruction to the device. For illustration purposes, the following descriptions are provided with reference to a remote control device of a medical device. It is understood that it is not intended to be limiting. Embodiments of the remote control device described herein may be applied in various devices other than those exemplified in the present disclosure.

Safety Regulations of International Electrotechnical Commission (IEC) 60601-2-1 (2009 edition) specify that at least one of switches involved in controlling a medical device (e.g., controlling a motion of a component of the medical device) shall be hard-wired or have an equivalent safety switching function. As used herein, if a switch is part of a remote control device and some safety measures are carried out to prevent a misoperation of a device, e.g., a medical device, caused by software errors and/or wireless transmission issues, the switch may be regarded as having an equivalent safety switching function.

Some companies have developed solutions to control the medical device via a remote control device. However, these conventional solutions often use a safety switching circuit that operates separately from the main remote control device and transmits a safety signal via a separate wireless channel using a separate wireless transmitter. One of the drawbacks of the conventional solutions is that it needs two separate wireless transmitter/receiver pairs, one for connecting the remote control device and the medical device and the other one for connecting the separate safety switching circuit and the medical device.

An aspect of the present disclosure provides a system for controlling a medical device (e.g., a radiotherapy (RT) device, a computed tomography (CT) device, a magnetic resonance imaging (MRI) device). The system may include a remote control device and a safety control device communicating with each other via a wireless connection. The remote control device may be configured to remotely control the medical device. The remote control device may include a switch (also referred to as a motion enable switch), a motion enable unit, and a hand control unit. The motion enable unit may be configured to generate processed information (e.g., an encrypted code, a decrypted code) by processing information (e.g., a code) using a first secret. The hand control unit may be capable of acquiring the processed information from the motion enable device only when the switch is in a closed state. Further, the hand control unit may be configured to transmit the processed information to the safety control device via the wireless connection. The safety control device may include a communication unit and a safety control unit. The communication unit may be configured to receive the processed information via the wireless connection. The safety control unit may be configured to verify the closed state of the switch by processing the processed information using a second secret that matches the first secret. Further, the safety control unit may be configured to enable control of the medical device when the closed state of the switch is verified.

According to some embodiments of the present disclosure, the system for controlling the medical device (or referred to as a medical control system) may include two parts, the remote control device and the safety control device. The hand control unit of the remote control device may be accessible to acquire the processed information from the motion enable device only when the switch is in a closed state, so that the medical device can be safely immobilized unless the motion enable switch is pressed by a user (e.g., a doctor). The safety control unit of the safety control device may verify the closed state of the switch by processing (e.g., encrypting or decrypting) the processed information passed between the two parts using the second secret that matches the first secret. The first secret and the second secret may be stored in hardware of the two parts and not known to any software, so that it is unlikely for any software errors or wireless transmission issues to send a valid signal to the medical device, therefore "the equivalent safety switching function" required in the safety regulations of IEC 60601-2-1 (2009 edition) may be realized. In addition, in some embodiments of the present disclosure, the remote control device and the switch may be connected to the safety control device via a single wireless connection (e.g., using a single wireless transmitter/receiver pair). Compared with conventional approaches that need two separate wireless transmitter/receiver pairs, the medical control system of the present disclosure is simpler in structure and efficient.

FIG. 1 is a schematic diagram illustrating an exemplary medical control system according to some embodiments of the present disclosure. As illustrated, the medical control system 100 may include a medical device 110, a network 120, and a control device 130. The medical control system 100 may be used to control the medical device 110 via the control device 130. The components of the medical control system 100 may be connected in one or more of various ways.

The medical device 110 may be configured to scan and/or treat an object (e.g., a patient). In the present disclosure, "object" and "object" are used interchangeably. The object may include any biological object (e.g., a human being, an animal, a plant, or a portion thereof) and/or a non-biological object (e.g., a phantom). For example, the object may include a specific portion of a body, such as the head, the thorax, the abdomen, or the like, or a combination thereof, of the object.

In some embodiments, the medical device 110 may be or include an imaging device. The imaging device may be configured to acquire imaging data relating to an object. For example, the imaging device may scan the object or a portion thereof that is located within its detection region and generate imaging data relating to the object or the portion thereof. The imaging data relating to the object may include an image, projection data, or a combination thereof. In some embodiments, the imaging data may include two-dimensional (2D) imaging data (e.g., a slice image), three-dimensional (3D) imaging data, four-dimensional (4D) imaging data (a series of 3D images over time), or the like, or any combination thereof.

In some embodiments, the imaging device may include a single modality imaging device. For example, the imaging device may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device, an ultrasonography scanner, a digital radiography (DR) scanner, or the like, or any combination thereof. In some embodiments, the imaging device may include a multi-modality imaging device. Exemplary multi-modality imaging devices may include a PET-CT device, a PET-MR device, or the like, or a combination thereof.

In some embodiments, the medical device 110 may be or include a treatment device (e.g., an RT device). The treatment device may be configured to deliver a radiotherapy treatment to an object. For example, the treatment device may deliver one or more radiation beams to a treatment region (e.g., a tumor) of an object for causing an alleviation of the object's symptom. In some embodiments, the treatment device may include a conformal radiation therapy device, an image-guided radiation therapy (IGRT) device, an intensity-modulated radiation therapy (IMRT) device, an intensity-modulated arc therapy (IMAT) device, an emission guided radiation therapy (EGRT), or the like, or a combination thereof.

For example, the medical device 110 may be an IGRT device. The IGRT device may be configured to acquire image data relating to the object and perform a radiotherapy treatment on the object. For example, as illustrated in FIG. 1, the medical device 110 may include an imaging component 111 and a treatment component 112. The imaging component 111 may be configured to acquire an image of the object before a radiotherapy treatment, during the radiotherapy treatment, and/or after the radiotherapy treatment. The treatment component 112 may be configured to deliver a radiotherapy treatment to the object. In some embodiments, the treatment component 112 may include a treatment radiation source, a gantry, a collimator, or the like, or any combination thereof. The treatment radiation source may be configured to emit treatment radiations toward the object. For example, the treatment radiation source may include a linear accelerator (LINAC). The collimator may be configured to control the shape of the treatment radiations generated by the treatment radiation source. In some embodiments, the treatment component 112 may be integrated into the imaging component 111.

The control device 130 may be configured to control the medical device 110. For example, the control device 130 may control the treatment component 112 to deliver a radiotherapy treatment to the object. As another example, the control device 130 may control the LINAC of the treatment component 112 to accelerate the treatment radiations emitted by the treatment radiation source. As a further example, the control device 130 may control the collimator of the treatment component to change the shape of the treatment radiations generated by the treatment radiation source. As a still further example, a patient may lie on a scanning table (or referred to as couch) of the medical device 110, and the control device 130 may control the scanning table to move the patient to a certain position.

The control device 130 may be connected to the medical device 110 via the network 120 so as to communicate information and/or data with the medical device 110. For example, the control device 130 may obtain data (e.g., scan data) from the medical device 110 via the network 120. As another example, the control device 130 may transmit a control instruction to the medical device 110 via the network 120. The network 120 may include any suitable network that can facilitate the exchange of information and/or data for the medical control system 100. In some embodiments, one or more components (e.g., the medical device 110, the control device 130) of the medical control system 100 may communicate information and/or data with one or more external resources (e.g., an external database) via the network 120. The network 120 may be and/or include a public network (e.g., the Internet), a private network (e.g., a local area network (LAN), a wide area network (WAN), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points, such as base stations and/or Internet exchange points, through which one or more components of the medical control system 100 may be connected to the network 120 to exchange data and/or information.

In some embodiments, the network 120 may include a wireless network that can establish a wireless connection between the control device 130 and the medical device 110. Merely by way of example, the wireless connection may include a wireless protocol (e.g., an 802.11 protocol, a Wi-Fi, a WiMax, etc.), a wireless radio, a wireless local area network (WLAN), a Bluetooth™, a ZigBee™ network, a near field communication (NFC), a mobile communication technology (e.g., 2G, 3G, 4G, 5G, etc.), or the like, or any combination thereof. In such cases, the control device 130 may be referred to as a remote control device of the medical device 110.

In some embodiments, the control device 130 may include a switch. A user may need to press the switch when or after he/she inputs an instruction for controlling the medical device 110 via the control device 130. Conventionally, if the switch is pressed, the instruction may be transmitted from the control device 130 to the medical device 110, and the medical device 110 may be controlled according to the instruction. However, if the medical device 110 and the control device 130 are connected to each other wirelessly, software errors and/or wireless transmission issues may occur, affecting the integrity and/or validity of information transmitted from the control device 130 to the medical device 110. For example, due to software errors of the control device 130, a control instruction may be accidentally generated and transmitted to the medical device 110 when the switch is not pressed. Therefore, it is desired to provide more reliable systems and methods for controlling the medical device 110 wirelessly, thereby avoiding misoperation caused by software errors or wireless transmission issues and improving the system safety.

Figure 2:
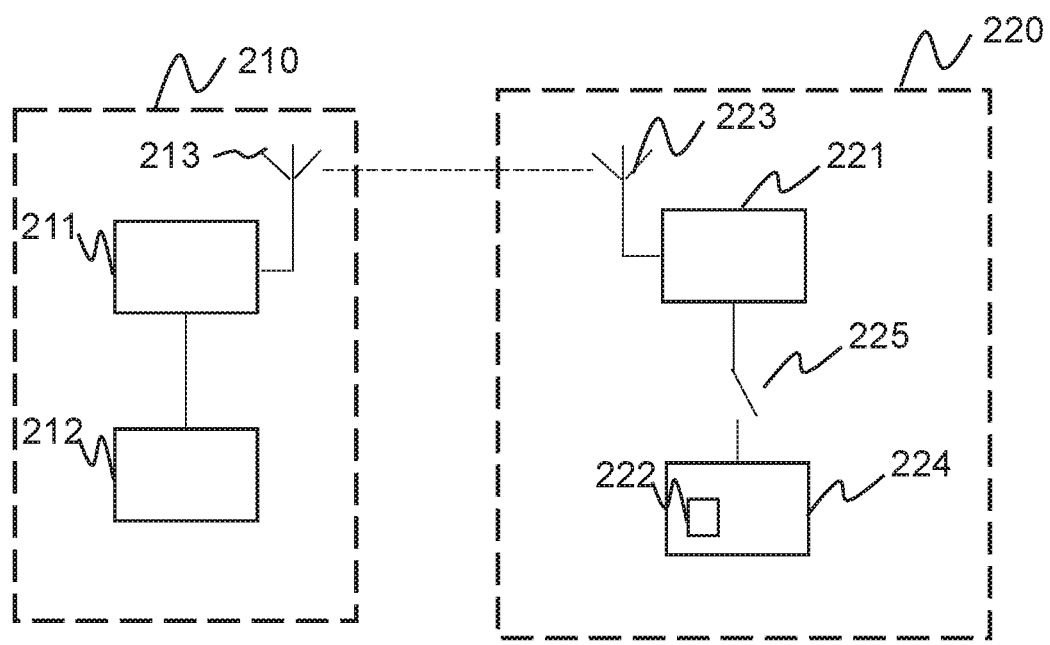
FIG. 2 is a block diagram illustrating an exemplary medical control system according to some embodiments of the present disclosure.

FIG. 2 provides a block diagram illustrating an exemplary medical control system 200 according to some embodiments of the present disclosure. As shown in FIG. 2, the medical control system 200 may include a remote control device 220 and a safety control device 210 communicate with each other via a wireless connection.

The remote control device 220 may be an exemplary embodiment of the control device 130 as described in connection with FIG. 1. The remote control device 220 may be configured to remotely control a medical device (e.g., the medical device 110). The safety control device 210 may be configured to control one or more devices (e.g., mechanical actuators) that can drive the medical device (or a portion thereof) to perform a certain operation. For example, the safety control device 210 may control a motor that can drive a gantry of the medical device to rotate. In some embodiments, the safety control device 210 may be part of the medical device or a separate device connected to the medical device via a wired connection.

The remote control device 220 may include a hand control unit 221, a communication unit 223, a motion enable unit 224, and a switch 225. The hand control unit 221 may provide one or more interactive elements. For example, the hand control unit 221 may include one or more input elements, such as a touch screen, a keyboard, a microphone, for a user to input an instruction for controlling the medical device. In some embodiments, the input element(s) may include a physical element (e.g., a button), and the user may cause a scanning table of the medical device to move by pressing the button. Additionally or alternatively, the input element(s) may include a virtual element (e.g., an icon of a key, or referred to as a virtual key, displayed on an interface of the hand control unit 221), and the user may cause a radiation source of the medical device to emit radiation rays by touching the virtual key.

In some embodiments, the hand control unit 221 may include a mobile device, a tablet computer, a laptop computer, or the like, or any combination thereof. In some embodiments, the mobile device may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the smart mobile device may include a mobile phone, a personal digital assistant (PDA), a gaming device, a navigation device, a point of sale (POS) device, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the hand control unit 221 may be implemented by a computing device 700 including one or more components as described in FIG. 7 and/or a mobile device 800 including one or more components as described in FIG. 8.

The switch 225 may need to be pressed (i.e., to become closed or turn to a closed state) by a user if the user wants to control the medical device 110 via the remote control device 220. The state of the switch 225 may affect the connection between the hand control unit 221 and the motion enable unit 224 as shown in FIG. 2. For example, if the switch 225 is in a closed state, the hand control unit 221 may be electrically connected to the motion enable unit 224 and capable of acquiring information from or transmitting information to the motion enable unit 224. If the switch 225 is in an open state, the hand control unit 221 may be disconnected from the motion enable unit 224 and not capable of acquiring information from or transmitting information to the motion enable unit 224. In some embodiments, the switch 225 may be a physical key on the motion enable unit 224. In some embodiments, the remote control device 220 may include a plurality of switches 225, e.g., two switches 225. The motion enable unit 224 and the hand control unit 221 may be connected to each other only when all switches 225 are pressed.

In some embodiments, the motion enable unit 224 may include a storage device 222. The storage device 222 may be configured to store data, instructions, and/or any other information. In some embodiments, the storage device 222 may store data obtained from the medical device, the motion enable unit 224, and/or the hand control unit 221. In some embodiments, the storage device 222 may store data and/or instructions that the remote control device 220 may execute or use to perform exemplary methods described in the present disclosure. In some embodiments, the storage device 222 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc.

In some embodiments, the storage device 222 may be configured to store a first secret. As used herein, a secret refers to information (e.g., an algorithm) that can be used for data encryption, data decryption, data validation, or the like, or any combination thereof. Merely by way of example, the first secret may be a hash function, a hash table, a private key, or a public key. The hash function refers to an algorithm to be applied to encrypt or decrypt information/data (e.g., a sequence of numbers or characters). The hash table refers to a predefined map (e.g., a static table) used to encrypt or decrypt the information/data (e.g., a sequence of numbers or characters). For example, the hash table may encrypt the information/data by mapping the information/data to an equivalent encrypted information/data by looking up a mapping table. Further, the hash table may decrypt the equivalent encrypted information/data by performing a reverse look up on the mapping table. In some embodiments, the storage device 222 may be omitted. In such cases, the motion enable unit 224 may a device with memory function and the first secret may be stored in the motion enable unit 224.

In some embodiments, the motion enable unit 224 may be configured to generate processed information by processing information using the first secret. For example, the motion enable unit 224 may encrypt or decrypt the information using the first secret. The information processed by the motion enable unit 224 may include information generated by the motion enable unit 224 itself and/or information generated by one or more other components (e.g., the safety control unit 212 of the safety control device 210). For example, the information may include a code or an encrypted code generated by the safety control unit 212. In some embodiments, the information processed by the motion enable unit 224 may include data relating to the medical device, data relating to the state (e.g., the closed state, an open state) of the switch 225, and other data. For example, the information may include a code or an encrypted code that includes a timestamp, an ID of the medical device, and an ID of the medical control system 200. In some embodiments, the information processed by the motion enable unit 224 may be stored in the form of a data packet that can be transmitted over a wireless protocol (e.g., WiFi, Bluetooth, etc.). More descriptions regarding the information processed by the motion enable unit 224 may be found elsewhere in the present disclosure. See, e.g., FIGS. 3-6, and relevant descriptions thereof. In some embodiments, the motion enable unit 224 may include a hardware circuit without software, such as a field-programmable gate array (FPGA) without software. This may prevent a misoperation of the medical device caused by software errors.

When the switch 225 is in a closed state (i.e., the switch 225 is pressed), the hand control unit 221 may be capable of acquiring the processed information from the motion enable device 224. Further, the hand control unit 221 may be configured to transmit the processed information to the safety control device 210 via the wireless connection between the safety control device 210 and the remote control device 220. For example, the hand control unit 221 may cause a communication unit 223 (e.g., an antenna) to transmit the processed information to the safety control device 210. The communication unit 223 may be an independent device or part of the hand control unit 221. In some embodiments, the hand control unit 221 and the motion enable unit 224 may be connected to each other via a wired connection. The wired connection may be achieved by, for example, an electric wire (e.g., a telephone wire), an optical cable (e.g., an optical fiber), a USB interface, or the like, or any combination thereof. For example, the hand control unit 221 may be a mobile device (e.g., a mobile device 800 shown in FIG. 8) and the motion enable unit 224 may be a shell or a dock (e.g., a charging dock) connected to the hand control unit 221 via a USB interface. In some embodiments, the motion enable unit 224 may be integrated into the hand control unit 221.

The safety control device 210 may include a control computer 211, a safety control unit 212, and a communication unit 213. The communication unit 213 may be paired with the communication unit 223 and configured to receive the processed information from the hand control unit 221 via the wireless connection between the safety control device 210 and the remote control device 220. In some embodiments, the control computer 211 may be a treatment control computer (TOO). The TCC may include control software (CSW). The CSW may receive the processed information from the communication unit 213 and transmit the processed information to the safety control unit 212. In some embodiments, the communication unit 213 may be an independent device or part of the control computer 211. In some embodiments, the control computer 211 may be an independent device or part of the safety control unit 212. In some embodiments, the control computer 211 may be omitted.

The safety control unit 212 may be configured to verify the closed state of the switch 225 by processing the processed information using a second secret that matches the first secret. Merely by way of example, the first secret may be a hash function, and the second secret may be a hash function that is the same as the hash function corresponding to the first secret. As another example, the first secret may be a private key and the second secret may be a public key matching the private key. In some embodiments, the safety control device 210 may include a storage device. The storage device may store the second secret and the safety control unit 212 may acquire the second secret from the storage device. In some embodiments, the safety control unit 212 may generate a processing result based on the processed information by performing data encryption, data decryption, data comparison, or the like, or any combination thereof. Further, the safety control unit 212 may verify the integrity and/or the authenticity of the processed information based on the processing result to verify the closed state of the switch 225. Merely by way of example, if the integrity and/or the authenticity of the processed information are verified, the safety control unit 212 may determine that the switch 225 is closed; if the integrity and/or the authenticity of the processed information are not verified, the safety control unit 212 may determine that the switch 225 is open. More descriptions regarding the verification of the closed state of the switch 225 may be found elsewhere in the present disclosure. See, e.g., FIGS. 3-6 and relevant descriptions thereof.

Further, the safety control unit 212 may be configured to enable control of the medical device when the closed state of the switch 225 is verified. For example, when the closed state of the switch 225 is verified, the safety control unit 212 may cause the medical device to perform certain operation(s). For example, the safety control unit 212 may cause a radiation source of the medical device to emit radiation rays. As another example, the safety control unit 212 may cause a scanning table of the medical device to move to a certain position.

In some embodiments, the safety control unit 212 may include an ancillary control box unit (ACBU) (e.g., a printed circuit board assembly (PCBA)). The ACBU may have an interface connected to one or more safety lines (e.g., a motion enable line) of the medical device, wherein the safety line(s) may be used to control one or more components (e.g., a mechanical actuator) of the medical device. In some embodiments, the safety control unit 212 may include an FPGA without software. For example, the FPGA of the safety control unit 212 may store a decryption algorithm or a hash function and be configured to decrypt the processed information received from the remote control device 220 using the decryption algorithm or the hash function. In some embodiments, the safety control device 210 may further include at least one communication relay station between the control computer 211 and the safety control unit 212. The at least one communication relay station may be configured to receive the processed information from the control computer 211 and forward the processed information to the safety control unit 212.

In some embodiments, the remote control device 220 may be able to control the medical device only if the switch 225 is closed continuously, and a continuous closed state of the switch 225 may need to be monitored. In some embodiments, to monitor the continuous closed state of the switch 225, the motion enable unit 224 may be further configured to generate updated processed information by processing the updated information using the first secret. The hand control unit 221 may then transmit the updated processed information to the safety control device 210 via the wireless connection. The communication unit 213 may receive the updated processed information via the wireless connection. The safety control unit 212 may verify the closed state of the switch 225 by processing the updated processed information using the second secret. If the switch 225 is still in the closed state, the safety control unit 212 may continue enabling the control of the medical device. If the switch 225 is found to be open, the safety control unit 212 may disable the control of the medical device.

Merely by way of example, the information processed by the motion enable unit 224 may be obtained or generated at a first time point, and updated information may be obtained or generated by the motion enable unit 224 at a second time point after the first time point. After the updated information is obtained or generated, the original information processed by the motion enable unit 224 may become invalid. Therefore, if the switch 225 is found to be open or the wireless connection between the remote control device 220 and the safety control device 210 becomes inoperable, the control of the medical device may be disabled at the second time point. In some embodiments, updated information may be obtained or generated by the motion enable unit 224 continuously or intermittently (e.g., periodically), such that the closed state of the switch 225 may be monitored continuously or intermittently (e.g., periodically). For example, the motion enable unit 224 may generate or obtain a new code every 50 milliseconds.

In some embodiments, data encryption and/or data decryption disclosed in the present disclosure may be performed according to a cryptography algorithm, such as a symmetric cryptography algorithm (e.g., an advanced encryption standard (AES), a data encryption standard (DES)), an asymmetric cryptography algorithm (e.g., a diffie-hellman key exchange/agreement algorithm, an RSA algorithm), a hash algorithm (e.g., a message-digest (MD) algorithm, a cyclic redundancy check, a murmurHash), or the like, or any combination thereof. For example, when a symmetric cryptography algorithm is used, the first secret and the second secret may be the same and can be used for both data encryption and data decryption. As another example, when an asymmetric cryptography algorithm is used, the first secret and the second secret may be one of a public/provide key pair. Merely by way of example, the first secret may be a private key and the second secret may be a public key. As a further example, when a hash algorithm is used, the first secret and the second secret may be the same hash function or hash table that are aligned (paired/agreed to) using a secret generator (e.g., a random number generator) in the start (e.g., start of day) of the transmission between the remote control device 220 and the safety control device 210. In some embodiments, for more advanced security, a complex encryption and decryption manner may be used such that it is difficult for a component (e.g. a hacker or malicious software) to intentionally generate valid information (e.g., an encrypted code) that can control the medical device in an unauthorized way.

In some embodiments, during an initial set-up of the medical control system 200, a pairing process may be performed to generate the first secret and the second secret. In some embodiments, a secret may be generated by, for example, one of the motion enable unit 224 and the safety control unit 212. The secret may serve as the first secret stored in the storage device 222 and also the second secret stored in the storage device of the safety control device 210. In some embodiments, the safety control unit 212 may generate the second secret and store the second secret in the storage device in the safety control device 210. Further, the motion enable unit 224 may generate the first secret based on the second secret and store the first secret in the storage device 222. For example, the safety control unit 212 may generate a random seed and use the random seed as the second secret. The safety control unit 212 may transmit the random seed to the control computer 211 and the control computer 211 may further transmit the random seed to the hand control unit 221 via the wireless connection. The motion enable unit 224 may receive the random seed from the hand control unit 221 and generate the first secret by using the random seed as part of the first secret.

According to some embodiments of the present disclosure, the motion enable unit 224 and the safety control unit 212 may be hardware circuits (e.g., FPGAs) without software. The processed information may be only accessible to the hand control unit 221 when the switch 225 in a closed state. The opening of the switch 225 may cause the hand control unit 221 to be physically disconnected from the motion enable unit 224 and accordingly unavailability of the processed information to the hand control unit 221. The first secret and the second secret may be unknown to any component with software (e.g., the hand control unit 221, the control computer 211). This may prevent safety issues (abnormal control of the medical device) caused by software errors or wireless transmission issues. Therefore, hardware grade security may be achieved even when the transmission path between the remote control device 220 and the safety control device 210 is controlled by software, and it is unlikely for a component with software to accidentally generate a valid control signal.

Moreover, in some embodiments, the hand control unit 221 may be implemented on a mobile device, such as an off-the-shelf Android or iOS phone, a tablet computer, or the like. One of the advantages of the remote control device 220 as described herein is that no custom or special hardware needs to be implemented to support the hand control unit 221 itself. The motion enable unit 224 may offer the processed information (e.g., an encrypted message) to the hand control unit 221 via the wired connection only when the switch 225 is in a closed state. For example, when the switch 225 is in the closed state, the motion enable unit 224 may transmit the encrypted message to an off-the-shelf device through a standard interface readily available on the off-the-shelf device, for example, USB, serial, i2c, NFC, Bluetooth, or the like. Therefore, a hardware grade security (or an equivalent safety switching function) can be achieved without any special custom hardware in the hand control unit 221 or the involved wireless transmitters (e.g., the communication unit 213, the communication unit 223) themselves.

It should be noted that the above descriptions of the medical control system 200 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, the medical control system 200 may include one or more other modules and/or one or more modules described above may be omitted. Additionally or alternatively, two or more components of the medical control system 200 may be integrated into a single component. A component of the medical control system 200 may be implemented on two or more sub-components. For example, the switch 225 may be integrated into the motion enable unit 224. In some embodiments, the switch 225, the storage device 222, and the motion enable unit 224 may be part of a same integrated circuit board or a chip.

In some embodiments, the closed state of the switch 225 may be monitored by a challenge and response process including a challenging stage and a response stage. The information processed by the motion enable unit 224 may be obtained from the safety control device 210. For example, in the challenge stage, the safety control unit 212 may obtain (e.g., by generating or retrieving from a storage device) the information and transmit the information to the motion enable unit 224. In the response stage, the motion enable unit 224 may generate the processed information using the first secret and transmit the processed information to the safety control unit 212. The safety control unit 212 may further verify the closed state of the switch 225 based on the processed information. In some embodiments, the challenge and response process may be executed multiple times, e.g., periodically, to verify a continuous closed state of the switch 225. In some embodiments, the time interval between two consecutive challenge and response processes may be less than a human reaction time (e.g., 300 milliseconds).

Figure 3:
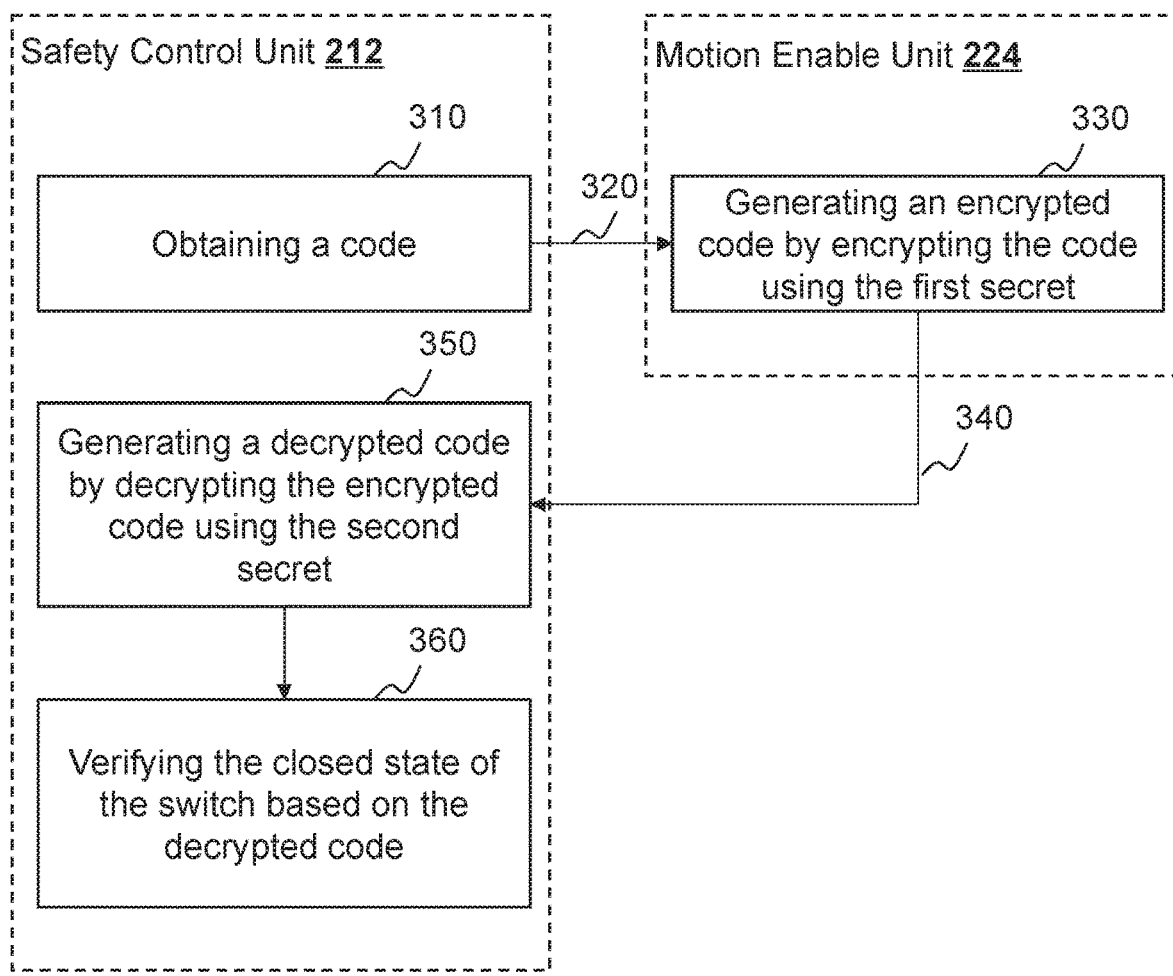
FIG. 3 is a flowchart illustrating an exemplary challenge and response process for verifying a closed state of a switch according to some embodiments of the present disclosure.

FIG. 3 is a flowchart illustrating an exemplary challenge and response process for verifying a closed state of a switch according to some embodiments of the present disclosure. For illustration purposes, the implementation of process 300 on the medical control system 200 is described as an example.

In 310, the safety control unit 212 may obtain a code.

In some embodiments, the code may be a random code. In some embodiments, the code may include a timestamp (e.g., the time point when the code is generated), an ID of the medical device, and an ID of the medical control system 200. Merely by way of example, the code may be a 32-byte code like: "YYYYMMD-DHHmmSSmmmXXXXXXXXXXXXXAA," wherein "YYYYMMDDHHmmSSmmmYYY" may be a timestamp, "XXXXXXXXXXXXX" may include data such as the installation information of the medical device and/or the ID of the medical control system 200, "AA" may be a 256-bit seed or a session key. Further, "YYYY" may be year, "MM" may be month, "DD" may be day, "HH" may be hour, "mm" may be minute, "SS" may be second, and "mmm" may be millisecond.

In some embodiments, the code may be generated by the safety control unit 212. For example, the safety control unit 212 may generate a random code at regular intervals (e.g., every 50 milliseconds). As another example, the code may be previously generated by the safety control unit 212 (or another device) and stored in a storage device (e.g., the storage device in the safety control unit 212, an external storage device). The safety control unit 212 may retrieve the code from the storage device.

In 320, when the switch 225 is in a closed state, the safety control unit 212 may transmit the code to the motion enable unit 224. For example, the safety control unit 212 may transmit the code to the control computer 211, and the control computer 211 may cause the communication unit 213 to transmit the code to the communication unit 223 of the remote control device 220 via a wireless connection between the safety control device 210 and the remote control device 220. Further, the hand control unit 221 may receive the code from the communication unit 223 and forward the code to the motion enable unit 224 when the switch 225 is in the closed state.

In 330, the motion enable unit 224 may generate an encrypted code by encrypting the code using the first secret. For example, the motion enable unit 224 may acquire the first secret from the storage device 222 and encrypt the code using the first secret. In some embodiments, the encryption of the code may be performed based on a cryptography algorithm (e.g., a symmetric encryption or an asymmetric cryptography algorithm) as described elsewhere in this disclosure (e.g., FIG. 2 and the relevant descriptions). For example, the first secret may be a private key and the motion enable unit 224 may encrypt the code using the private key.

In 340, when the switch 225 is in the closed state, the motion enable unit 224 may transmit the encrypted code to the safety control unit 212. For example, when the switch 225 is in the closed state, the motion enable unit 224 may transmit the encrypted code to the hand control unit 221, and the hand control unit 221 may cause the communication unit 223 to transmit the encrypted code to the communication unit 213 of the safety control device 210 via the wireless connection between the safety control device 210 and the remote control device 220. Further, the control computer 211 may receive the encrypted code from the communication unit 213 and forward the encrypted code to the safety control unit 212.

In 350, the safety control unit 212 may generate a decrypted code by decrypting the encrypted code using the second secret.

In some embodiments, the decryption of the encrypted code may be performed based on a cryptography algorithm (e.g., a symmetric encryption or an asymmetric cryptography algorithm) as described elsewhere in this disclosure (e.g., FIG. 2 and the relevant descriptions). For example, the first secret may be a private key, the second secret may be a public key matching the private key, and the safety control unit 212 may decrypt the encrypted code using the public key.

In 360, the safety control unit 212 may verify the closed state of the switch 225 based on the decrypted code.

In some embodiments, the safety control unit 212 may verify the closed state of the switch 225 by comparing the decrypted code with the original code. If the decrypted code is the same as the original code, the safety control unit 212 may determine that the switch 225 is in the closed state and enable control of the medical device. If the decrypted code is different from the original code, the safety control unit 212 may determine that the switch 225 is not in the closed state and does not enable control of the medical device. Because only hardware (e.g., the safety control unit 212, the motion enable unit 224) in the medical control system 200 knows the first secret and the second secret, while the software (e.g., the hand control unit 221, the control computer 211) in the medical control system 200 does not know the first secret and the second secret, the closed state of the switch 225 may be verified by a match between the original code and the decrypted code.

In some embodiments, the remote control device 220 may include a first clock, and the safety control device 210 may include a second clock. The first clock and the second clock may be synchronized at the start of the medical control system 200 (e.g., at the beginning of a day or a treatment). In 330, the first clock may generate a first timestamp indicating a current time point when the first timestamp is generated. The motion enable unit 224 may generate the encrypted code by encrypting the code received from the safety control unit 212 and the first timestamp. In 350, the safety control unit 212 may decrypt the encrypted code to obtain the first timestamp. The second clock of the safety control device 210 may be configured to generate a second timestamp indicating a current time point when the encrypted code is received or decrypted. The safety control unit 212 may verify the closed state of the switch 225 by comparing the first timestamp of the decrypted code with the second timestamp. For example, the safety control unit 212 may a time difference between the first timestamp and the second timestamp. Further, the safety control unit 212 may verify the closed state of the switch 225 by determining whether the time difference is less than a threshold time (e.g., 50 or 100 milliseconds). The threshold time may be determined by taking a time needed for data transmission and other latencies into consideration. Merely by way of example, if the time difference is less than the threshold time, the safety control unit 212 may determine that the switch 225 is in the closed state and enable control of the medical device. If the time difference exceeds the threshold time, the safety control unit 212 may determine that the closed state of the switch 225 cannot be verified and does not enable control of the medical device.

In some embodiments, the threshold time may relate to the frequency of verifying the closed state of the switch 225. For example, the closed state of the switch 225 may need to be verified in every 50 milliseconds. In such cases, the safety control unit 212 may generate a new code every 50 milliseconds, and a previous code generated by the safety control unit 212 may become invalid. In verifying the closed state of the switch 225, if the difference between the timestamp of the decrypted code and the current timestamp exceeds 50 million seconds, the safety control unit 212 may determine that the code corresponding to the decrypted code becomes invalid and the closed state of the switch 225 cannot be verified.

Figure 4:
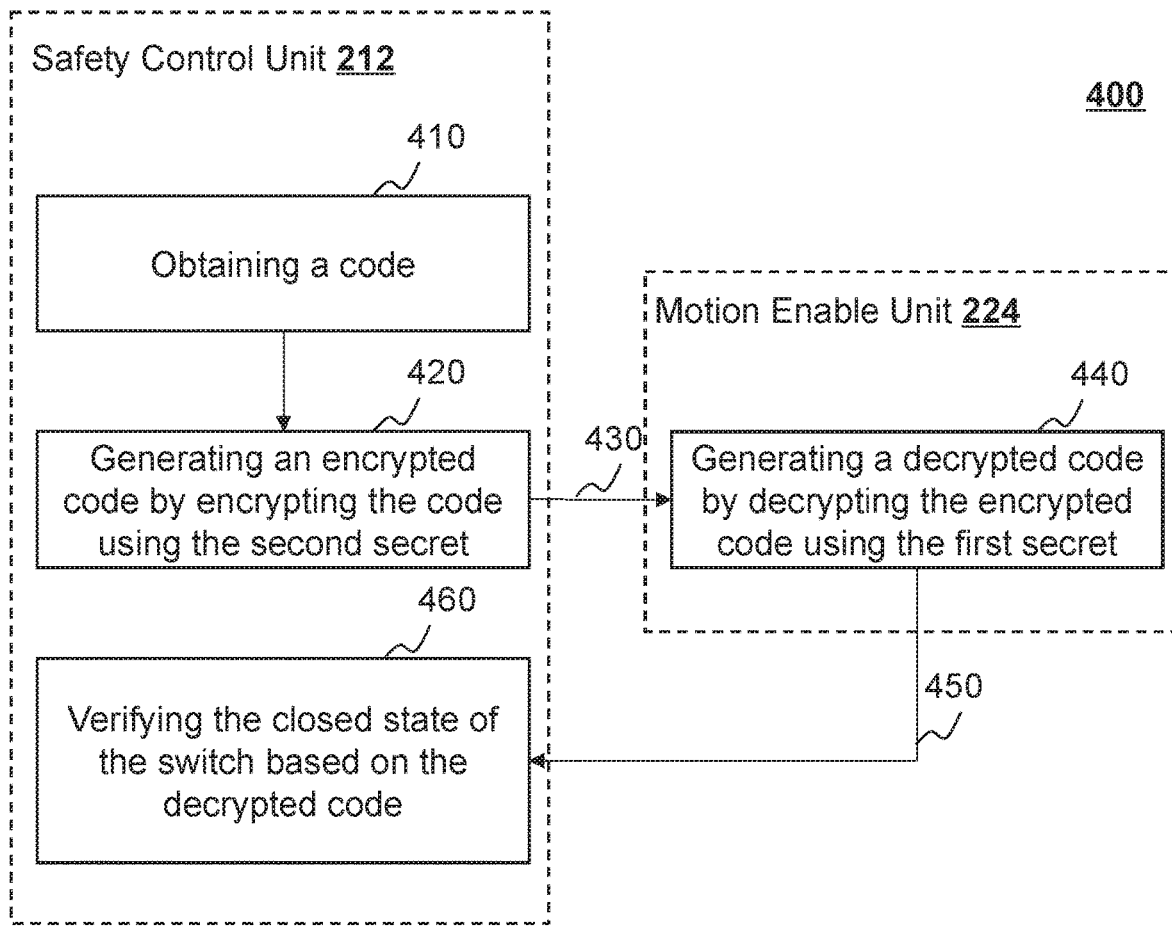
FIG. 4 is a flowchart illustrating another exemplary challenge and response process for verifying a closed state of a switch according to some embodiments of the present disclosure.

FIG. 4 is a flowchart illustrating another exemplary challenge and response process for verifying a closed state of a switch according to some embodiments of the present disclosure. For illustration purposes, the implementation of process 400 on the medical control system 200 is described as an example.

In 410, the safety control unit 212 may obtain a code. Operation 410 may be performed in a similar manner as operation 310 as described in connection with FIG. 3, and the descriptions thereof are not repeated here.

In 420, the safety control unit 212 may generate an encrypted code by encrypting the code using the second secret. In some embodiments, the encryption of the code may be performed based on a cryptography algorithm (e.g., a symmetric encryption, an asymmetric cryptography) algorithm as described elsewhere in this disclosure (e.g., FIG. 2 and the relevant descriptions). For example, the second secret may be a public key and the safety control unit 212 may encrypt the code using the public key.

In 430, when the switch 225 is in the closed state, the safety control unit 212 may transmit the encrypted code to the motion enable unit 224. For example, the safety control unit 212 may transmit the encrypted code to the control computer 211, and the control computer 211 may cause the communication unit 213 to transmit the encrypted code to the communication unit 223 of the remote control device 220 via a wireless connection between the safety control device 210 and the remote control device 220. Further, the hand control unit 221 may receive the encrypted code from the communication unit 223 and forward the encrypted code to the motion enable unit 224 when the switch 225 is in the closed state.

In 440, the motion enable unit 224 may generate a decrypted code by decrypting the encrypted code using the first secret. For example, the motion enable unit 224 may acquire the first secret from the storage device 222 and decrypt the encrypted code using the first secret. In some embodiments, the decryption of the encrypted code may be performed based on a cryptography algorithm (e.g., a symmetric encryption or an asymmetric cryptography algorithm) as described elsewhere in this disclosure (e.g., FIG. 2 and the relevant descriptions). For example, the first secret may be a private key and the motion enable unit 224 may decrypt the encrypted code using the private key.

In 450, when the switch 225 is in the closed state, the motion enable unit 224 may transmit the decrypted code to the safety control unit 212. For example, when the switch 225 is in the closed state, the motion enable unit 224 may transmit the decrypted code to the hand control unit 221, and the hand control unit 221 may cause the communication unit 223 to transmit the decrypted code to the communication unit 213 of the safety control device 210 via the wireless connection between the safety control device 210 and the remote control device 220. Further, the control computer 211 may receive the decrypted code from the communication unit 213 and forward the decrypted code to the safety control unit 212.

In 460, the safety control unit 212 may verify the closed state of the switch 225 based on the decrypted code. Operation 460 may be performed in a similar manner as operation 360 as described in connection with FIG. 3, and the descriptions thereof are not repeated here.

Figure 5:
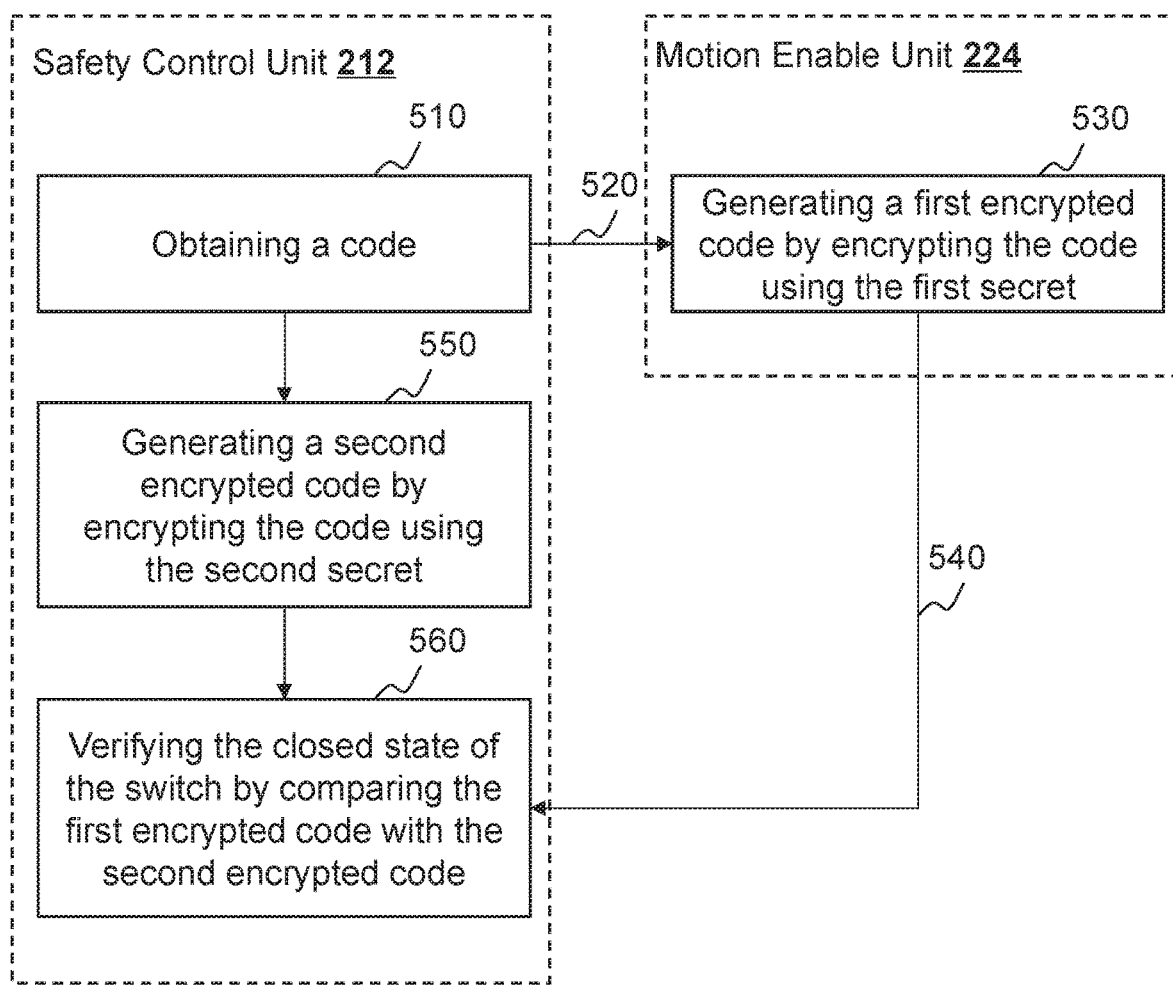
FIG. 5 is a flowchart illustrating another exemplary challenge and response process for verifying a closed state of a switch according to some embodiments of the present disclosure.

FIG. 5 is a flowchart illustrating another exemplary challenge and response process for verifying a closed state of a switch according to some embodiments of the present disclosure. For illustration purposes, the implementation of process 500 on the medical control system 200 is described as an example.

In 510, a safety control unit 212 may obtain a code. Operation 510 may be performed in a similar manner as operation 310 as described in connection with FIG. 3, and the descriptions thereof are not repeated here.

In 520, when the switch 225 is in the closed state, the safety control unit 212 may transmit the code to the motion enable unit 224. Operation 520 may be performed in a similar manner as operation 320 as described in connection with FIG. 3, and the descriptions thereof are not repeated here.

In 530, the motion enable unit 224 may generate a first encrypted code by encrypting the code using the first secret. For example, the motion enable unit 224 may acquire the first secret from the storage device 222 and encrypt the code using the first secret. In some embodiments, the encryption of the code using the first secret may be performed based on a cryptography algorithm as described elsewhere in this disclosure (e.g., FIG. 2 and the relevant descriptions). For example, the cryptography algorithm may be a hash algorithm. The first secret may be a hash function. The motion enable unit 224 may encrypt the code by converting the code into a hash table using the hash function.

In 540, when the switch 225 is in the closed state, the motion enable unit 224 may transmit the first encrypted code to the safety control unit 212. Operation 540 may be performed in a similar manner as operation 340 as described in connection with FIG. 3, and the descriptions thereof are not repeated here.

In 550, the safety control unit 212 may generate a second encrypted code by encrypting the code using the second secret. In some embodiments, the encryption of the code using the second secret may be performed based on the cryptography algorithm as described elsewhere in this disclosure (e.g., FIG. 2 and the relevant descriptions). For example, the cryptography algorithm may be a hash algorithm. The second secret may be a hash function that is the same as the hash function corresponding to the first secret. The safety control unit 212 may encrypt the code by converting the code into a second hash table using the hash function corresponding to the second secret.

In 560, the safety control unit 212 may verify the closed state of the switch 225 by comparing the first encrypted code with the second encrypted code. If the first encrypted code is the same as the second encrypted code, the safety control unit 212 may determine that the switch 225 is in the closed state and enable control of the medical device. If the first encrypted code is different from the second encrypted code, the safety control unit 212 may determine that the closed state of the switch 225 cannot be verified and does not enable control of the medical device.

In some embodiments, a challenge and response process (e.g., the process 300, the process 400, or the process 500) may be executed multiple times (e.g., continuously or intermittently (e.g., periodically)) to verify a continuous closed state of the switch 225. Taking the process 300 as an example, the safety control unit 212 may obtain a new code at regular intervals (e.g., every 30 or 50 milliseconds). When the switch 225 is still in a closed state, the safety control unit 212 may transmit the new code to the motion enable unit 224. The motion enable unit 224 may generate a new encrypted code by encrypting the new code using the first secret. When the switch 225 is still in a closed state, the motion enable unit 224 may transmit the new encrypted code to the safety control unit 212. The safety control unit 212 may generate a new decrypted code by decrypting the new encrypted code using the second secret. Further, the safety control unit 212 may verify the continuous closed state of the switch 225 based on the new decrypted code.

In some embodiments, the closed state of the switch 225 may be monitored by a one-way transmission process. In the one-way transmission process, both the motion enable unit 224 and the safety control unit 212 may obtain (e.g., generate) information, such as a code. The motion enable unit 224 may generate the processed information using the first secret and transmit the processed information to the safety control unit 212. The safety control unit 212 may verify the closed state of the switch 225 based on the processed information received from the motion enable unit 224 and the locally obtained information. A challenge and response process as described in connection with FIGS. 3-5 may involve information transmission from the safety control unit 212 to the motion enable unit 224 and information transmission from the motion enable unit 224 back to the safety control unit 212. Compared with the challenge and response process, the one-way transmission process may only involve one-way information transmission from the motion enable unit 224 to the safety control unit 212 and be more efficient. In some embodiments, the one-way transmission process may be executed multiple times to verify a continuous closed state of the switch 225.

Figure 6:
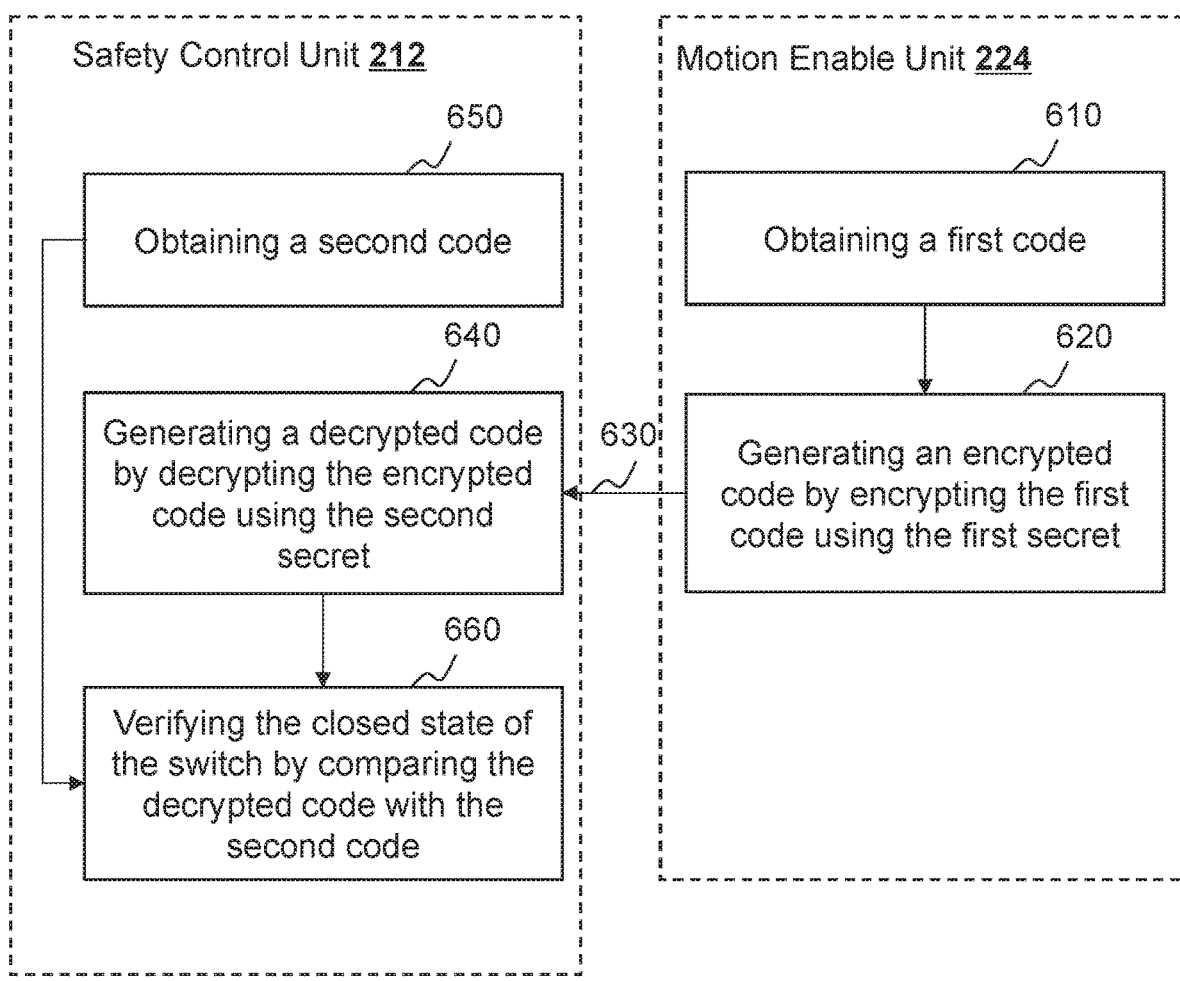
FIG. 6 is a flowchart illustrating an exemplary one-way transmission process for verifying a closed state of a switch according to some embodiments of the present disclosure.

FIG. 6 is a flowchart illustrating an exemplary one-way transmission process for verifying a closed state of a switch according to some embodiments of the present disclosure. For illustration purposes, the implementation of process 600 on the medical control system 200 is described as an example.

In 610, a motion enable unit 224 may obtain a first code. The obtaining of the first code may be performed in a similar manner as that of operation 310 as described in connection with FIG. 3, and the descriptions thereof are not repeated here.

In 620, the motion enable unit 224 may generate an encrypted code by encrypting the first code using the first secret. The generation of the encrypted code may be performed in a similar manner as that of operation 330 as described in connection with FIG. 3, and the descriptions thereof are not repeated here.

In 630, when the switch 225 is in a closed state, the motion enable unit 224 may transmit the encrypted code to the safety control unit 212. Operation 630 may be performed in a similar manner as operation 340 as described in connection with FIG. 3, and the descriptions thereof are not repeated here.

In 640, the safety control unit 212 may generate a decrypted code by decrypting the encrypted code using the second secret. The generation of the decrypted code may be performed in a similar manner as that of operation 350 as described in connection with FIG. 3, and the descriptions thereof are not repeated here.

In 650, the safety control unit 212 may obtain a second code. The second code has a same value as the first code. The obtaining of the second code may be performed in a similar manner as that of operation 310 as described in connection with FIG. 3, and the descriptions thereof are not repeated here.

In 660, the safety control unit 212 may verify the closed state of the switch 225 by comparing the decrypted code with the second code.

If the decrypted code is the same as the second code, the safety control unit 212 may determine that the switch 225 is in the closed state and enable control the medical device. If the decrypted code is different from the second code, the safety control unit 212 may determine that the switch 225 is not in the closed state and not enable the control of the medical device.

In some embodiments, the remote control device 220 may include a first clock, and the safety control device 210 may include a second clock. The first clock and the second clock may be synchronized at the start of the medical control system 200 (e.g., at the beginning of a day or a treatment). The verification of the closed state of the switch 225 may be performed based on timestamps generated by the first and second clocks during the one-way transmission process. For example, in 620, the first clock may be configured to generate a first timestamp indicating a current time point when the first timestamp is generated. The motion enable unit 224 may generate the encrypted code by encrypting the first code and the first timestamp. In 640, the safety control unit 212 may decrypt the encrypted code to obtain the first timestamp. The second clock of the safety control device 210 may be configured to generate a second timestamp indicating a current time point when the encrypted code is received or decrypted. The safety control unit 212 may verify the closed state of the switch 225 by comparing the first timestamp of the decrypted code with the second timestamp. More descriptions regarding the verification of the closed state of the switch may be found elsewhere in the present disclosure. See, e.g., FIG. 3 and relevant descriptions thereof.

In some embodiments, the process 600 may be continuously or intermittently (e.g., regularly) executed multiple times to verify a continuous closed state of the switch 225. In the first execution of the process 600, the first code and the second code may have a same starting value. During the subsequent execution (e.g., the 2th time) of the process 600, the first code may be generated by the motion enable unit 224 according to an updating scheme, the second code may be generated by the safety control unit 212 according to the same updating scheme. For example, the motion enable unit 224 may generate the first code by performing code updating at each of a series of time points according to the updating scheme, and the safety control unit 212 may generate the second code by performing code updating at each of the series of time points according to the updating scheme. In this way, the motion enable unit 224 and the safety control unit 212 may generate an identical code at each time point of the series of time points.

In some embodiments, the code updating performed by the motion enable unit 224 and the safety control unit 212 may be performed based on a same starting value using, for example, a timestamp generator or a pseudo-random number generator. For example, in each execution other than the first execution of the process 600, the motion enable unit 224 may generate a first code used in the execution by updating the timestamp of the first code used in a previous execution or the starting value used in the first execution with a current timestamp generated by a timestamp generator, and the safety control unit 212 may generate a second code used in the execution in a similar manner as how the first code used in the execution is generated. As another example, in each execution other than the first execution of the process 600, the motion enable unit 224 may generate a first code used in the execution by generating a random number using a pseudo-random number generator which is started with a common seed, and the safety control unit 212 may generate a second code used in the execution by generating a same random number using the pseudo-random number generator.

As described elsewhere in this disclosure, the switch 225 may need to be in a continuous closed state to enable continuous control of the medical device. Without the updating scheme as aforementioned, an unchanged first code and an unchanged second code may be used in each execution, which may go into an endless loop and simulate a continuous closed state of the switch 225. To protect against such faults, the first code and the second code may need to be updated frequently (e.g., every 50 milliseconds), so that a continuous closed state of the switch 225 can be proven regardless of any software faults.

Figure 7:
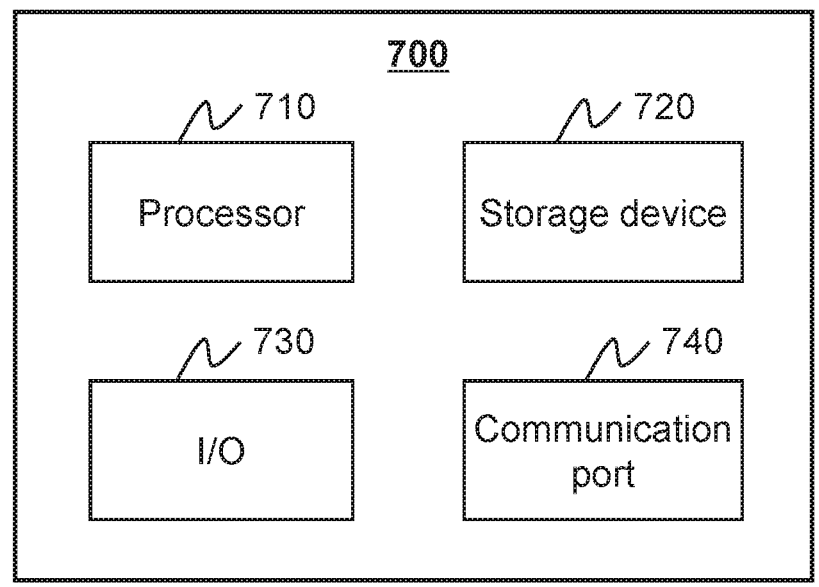
FIG. 7 is a schematic diagram illustrating exemplary hardware and/or software components of a computing device according to some embodiments of the present disclosure.

It should be noted that the above description regarding the process 300, the process 400, the process 500, and the process 600 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, a process may be accomplished with one or more additional operations not described and/or without one or more of the operations discussed above. For example, the process 300 may include an additional transmitting operation to transmit a control instruction to the medical device to enable the control of the medical device. In some embodiments, operations of a process may be performed in any order. Taking the process 600 as an example, operation 640 may be performed before or after operation 650, or operations 640 and 650 may be performed simultaneously. In some embodiments, both the motion enable unit 224 and the safety control unit 212 may obtain (e.g., by generating or retrieving) the information, such as the code. The motion enable unit 224 may generate the first processed information by processing (e.g., encrypting the code generated by the motion enable unit 224) the information using the first secret and transmit the first processed information to the safety control unit 212. The safety control unit 212 may generate the second processed information by processing (e.g., encrypting the code generated by the safety control unit 212) the information using the second secret. Further, the safety control unit 212 may verify the closed state of the switch 225 by comparing the first processed information received from the motion enable unit 224 and the second processed information, FIG. 7 is a schematic diagram illustrating exemplary hardware and/or software components of an exemplary computing device according to some embodiments of the present disclosure. The computing device 700 (or a portion thereof) may be used to implement a component of a medical control system (e.g., the medical control system 100, the medical control system 200) as described herein. For example, the control computer 211 and/or the hand control unit 221 may be implemented on the computing device 700, respectively, via its hardware, software program, firmware, or a combination thereof. As illustrated in FIG. 7, the computing device 700 may include a processor 710, a storage 720, an input/output (I/O) 730, and a communication port 740.

The processor 710 may execute computer instructions (e.g., program codes) and perform functions of the control device 130 (e.g., the hand control unit 221) in accordance with techniques described herein. The computer instructions may include, for example, routines, programs, objects, components, data structures, procedures, modules, and functions, which perform particular functions described herein. For example, the processor 710 may receive the processed information from the motion enable unit 224 and transmit the processed information to the safety control device 210.

In some embodiments, the processor 710 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 700. However, it should be noted that the computing device 700 in the present disclosure may also include multiple processors. Thus operations and/or method steps that are performed by one processor as described in the present disclosure may also be jointly or separately performed by the multiple processors. For example, if in the present disclosure the processor of the computing device 700 executes both operation A and operation B, it should be understood that operation A and operation B may also be performed by two or more different processors jointly or separately in the computing device 700 (e.g., a first processor executes operation A and a second processor executes operation B, or the first and second processors jointly execute operations A and B).

The storage 720 may store data/information obtained from the motion enable unit 224. In some embodiments, the storage 720 may include a mass storage device, a removable storage device, a volatile read-and-write memory, a read-only memory (ROM), or the like, or a combination thereof. In some embodiments, the storage 720 may store one or more programs and/or instructions to perform exemplary methods described in the present disclosure. For example, the storage 720 may store a program for the computing device 700 to execute to transmit the processed information to the safety control device 210. As another example, the storage 720 may store a program for the computing device 700 to execute to perform data decryption and/or data encryption.

The I/O 730 may input and/or output signals, data, information, etc. In some embodiments, the I/O 730 may enable a user interaction with the computing device 700. In some embodiments, the I/O 730 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof. In some embodiments, the I/O 730 may be omitted. In this case, the motion enable unit 224 and/or the safety control unit 212 may be implemented on the computing device 700.

The communication port 740 may be connected to a network (e.g., the network 120) to facilitate data communications. The communication port 740 may establish connections between the motion enable unit 224 and other components (e.g., the network 120) of the medical control system 100. The connection may be a wired connection, a wireless connection, any other communication connection that can enable data transmission and/or reception, and/or a combination of these connections. The wired connection may include, for example, an electric wire connection (e.g., a telephone wire), a fiber connection, a cable connection (e.g., an electrical cable, an optical cable), a USB interface connection, or the like, or any combination thereof. The wireless connection may include, for example, a wireless protocol (e.g., an 802.11 protocol, a Wi-Fi, a WiMax, etc.), a wireless radio, a wireless local area network (WLAN), a Bluetooth™, a ZigBee™ network, a near field communication (NFC), a mobile communication technology (e.g., 2G, 3G, 4G, 5G, etc.), or the like, or any combination thereof. In some embodiments, the communication port 740 may be and/or include a standardized communication port, such as RS232, RS485, etc. In some embodiments, the communication port 740 may be a specially designed communication port. For example, the communication port 740 may be designed in accordance with the digital imaging and communications in medicine (DICOM) protocol.

Figure 8:
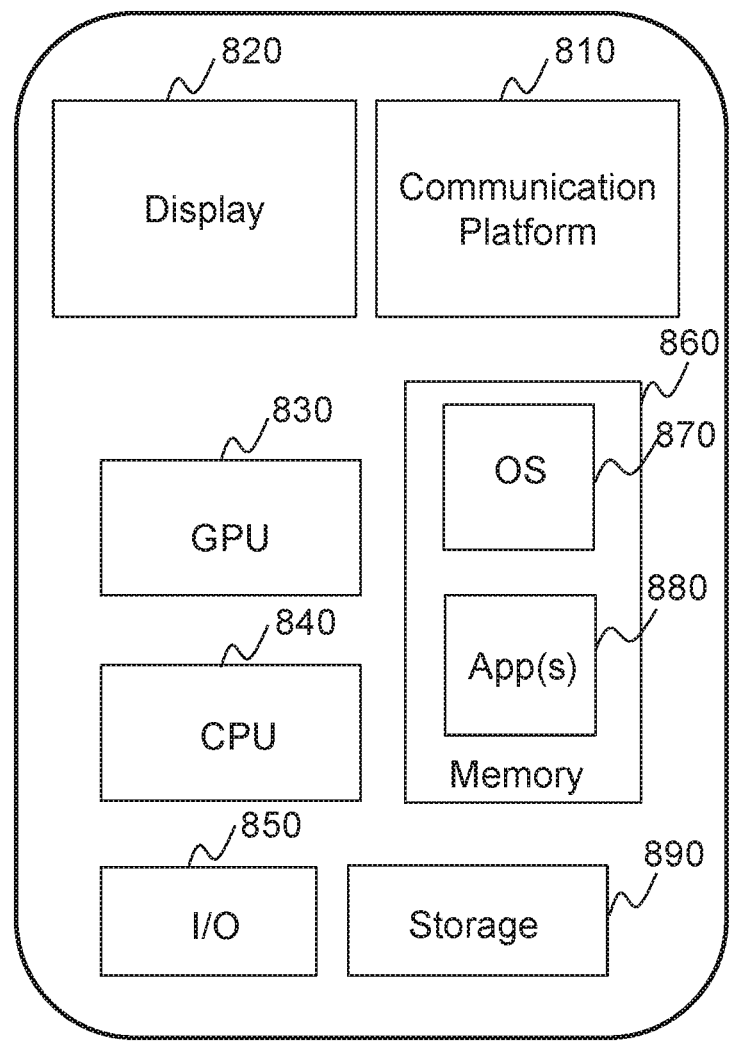
FIG. 8 is a schematic diagram illustrating exemplary hardware and/or software components of a mobile device according to some embodiments of the present disclosure.

FIG. 8 is a schematic diagram illustrating exemplary hardware and/or software components of an exemplary mobile device according to some embodiments of the present disclosure. In some embodiments, a component of a medical control system (e.g., the medical control system 100 or 200) (e.g., the hand control unit 221) may be implemented on one or more components of the mobile device 800.

As illustrated in FIG. 8, the mobile device 800 may include a communication platform 810, a display 820, a graphics processing unit (GPU) 830, a central processing unit (CPU) 840, an I/O 850, a memory 860, and a storage 890. In some embodiments, any other suitable component, including but not limited to a system bus or a controller (not shown), may also be included in the mobile device 800. In some embodiments, a mobile operating system 870 (e.g., iOS™, Android™, Windows Phone™, etc.) and one or more applications 880 may be loaded into the memory 860 from the storage 890 in order to be executed by the CPU 840. The applications 880 may include a browser or any other suitable mobile apps for receiving and rendering information relating to the medical control system 100. User interactions with the information stream may be achieved via the I/O 850 and provided to the control device 130 and/or other components of the medical control system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device. It is believed that those skilled in the art are familiar with the structure, programming and general operation of such computer equipment and as a result, the drawings should be self-explanatory.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the users computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for controlling a radiotherapy (RT) device, comprising:
   a remote control device and a safety control device communicating with each other via a wireless connection, wherein
   the remote control device is configured to remotely control the RT device and comprises:
      a switch configured to control a connection between a motion enable unit and a hand control unit;
      the motion enable unit configured to generate processed information by processing information using a first secret; and
      the hand control unit that is capable of acquiring the processed information from the motion enable device only when the switch is in a closed state and configured to transmit the processed information to the safety control device via the wireless connection, and
   the safety control device comprises:
      a communication unit configured to receive the processed information via the wireless connection, the communication unit including a wireless transmitter; and
      a safety control unit configured to verify the closed state of the switch by processing the processed information using a second secret that matches the first secret, and enable control of the RT device when the closed state of the switch is verified, wherein
the motion enable unit and the safety control unit are hardware circuits without software,
the switch is a physical key on the motion enable unit,
the hand control unit is a component with software,
the first secret and the second secret are respectively stored in the hardware circuits of the motion enable unit and the safety control unit, not known to any components with software, and the first secret and the second secret having been paired with each other during an initial set-up of the system,
the processed information is accessible to the software of the hand control unit only when the switch is in the closed state, and
an opening of the switch causes the hand control unit to be physically disconnected from the hardware circuit of the motion enable unit and accordingly causes unavailability of the processed information to the software of the hand control unit.

2. The system of claim 1, wherein the hand control unit and the motion enable unit are connected to each other via a wired connection.

3. The system of claim 1, wherein
the safety control unit is configured to obtain a code,
to generate the processed information, the motion enable unit is configured to generate an encrypted code by encrypting the code using the first secret, and
to verify the closed state of the switch, the safety control unit is configured to generate a decrypted code by decrypting the encrypted code using the second secret and compare the decrypted code with the code.

4. The system of claim 1, wherein
the safety control unit is configured to generate an encrypted code by encrypting a code using the second secret,
to generate the processed information, the motion enable unit is configured to generate a decrypted code by decrypting the encrypted code using the first secret, and
to verify the closed state of the switch, the safety control unit is configured to compare the decrypted code with the code.

5. The system of claim 1, wherein
the safety control unit is configured to obtain a code,
to generate the processed information, the motion enable unit is configured to generate a first encrypted code by encrypting the code using the first secret, and
to verify the closed state of the switch, the safety control unit is configured to generate a second encrypted code by encrypting the code using the second secret and compare the first encrypted code with the second encrypted code.

6. The system of claim 1, wherein
the motion enable unit is configured to obtain a first code,
to generate the processed information, the motion enable unit is configured to generate an encrypted code by encrypting the first code using the first secret, and
to verify the closed state of the switch, the safety control unit is configured to obtain a second code, generate a decrypted code by decrypting the encrypted code using the second secret, and compare the decrypted code with the second code, wherein the first code and the second code have a same value.

7. The system of claim 6, wherein each of the first code and the second code has a starting value.

8. The system of claim 6, wherein the first code is generated by the motion enable unit according to an updating scheme, and the second code is generated by the safety control unit according to the updating scheme.

9. The system of claim 8, wherein the updating scheme includes:
performing code updating at each of a series of time points.

10. The system of claim 9, wherein the updating is performed using, based on a starting value, a timestamp generator or a pseudo-random number generator.

11. The system of claim 1, wherein
the motion enable unit is further configured to generate updated processed information by processing updated information using the first secret,
the hand control unit is further configured to transmit the updated processed information to the safety control device via the wireless connection,
the communication unit is further configured to receive the updated processed information via the wireless connection; and
the safety control unit is further configured to verify the closed state of the switch by processing the updated processed information using the second secret and enable control of the RT device when the closed state of the switch is verified.

12. The system of claim 1, wherein the first secret and the second secret are the same.

13. The system of claim 1, wherein:
the first secret is a private key and the second secret is a public key; or
the first secret is the public key and the second secret is the private key.

14. A method for controlling a radiotherapy (RT) device, the method being implemented on a remote control device and a safety control device communicating with each other via a wireless connection, wherein
the remote control device is configured to remotely control the RT device and comprises a switch, a motion enable unit, and a hand control unit, the switch being configured to control a connection between the motion enable unit and the hand control unit, and
the safety control device comprises a communication unit and a safety control unit, the communication unit including a wireless transmitter, the method comprising:
generating, by the motion enable unit, processed information by processing information using a first secret;
acquiring, by the hand control unit, the processed information from the motion enable device only when the switch is in a closed state;
transmitting, by the hand control unit, the processed information to the safety control device via the wireless connection;
receiving, by the communication unit, the processed information via the wireless connection;
verifying, by the safety control unit, the closed state of the switch by processing the processed information using a second secret that matches the first secret; and
enabling control of the RT device when the closed state of the switch is verified, wherein
the motion enable unit and the safety control unit are hardware circuits without software, the switch is a physical key on the motion enable unit, the hand control unit is a component with software, the first secret and the second secret are respectively stored in the hardware circuits of the motion enable unit and the safety control unit, not known to any components with software, and the first secret and the second secret having been paired with each other during an initial set-up of the system, the processed information is accessible to the software of the hand control unit only when the switch is in the closed state, and an opening of the switch causes the hand control unit to be physically disconnected from the hardware circuit of the motion enable unit and accordingly causes unavailability of the processed information to the software of the hand control unit.

15. The method of claim 14, wherein the method further includes obtaining, by the safety control unit, a code, the generating, by the motion enable unit, processed information by processing information using a first secret comprises generating an encrypted code by encrypting the code using the first secret, and the verifying, by the safety control unit, the closed state of the switch-comprises generating a decrypted code by decrypting the encrypted code using the second secret and comparing the decrypted code with the code.

16. The system of claim 14, wherein the method further includes generating, by the safety control unit, an encrypted code by encrypting a code using the second secret, the generating, by the motion enable unit, processed information by processing information using a first secret comprises generating a decrypted code by decrypting the encrypted code using the first secret, and the verifying, by the safety control unit, the closed state of the switch-comprises comparing the decrypted code with the code.

17. The system of claim 14, wherein the method further includes obtaining, by the safety control unit, a code, the generating, by the motion enable unit, processed information by processing information using a first secret comprises generating a first encrypted code by encrypting the code using the first secret, and the verifying, by the safety control unit, the closed state of the switch-comprises generating a second encrypted code by encrypting the code using the second secret and comparing the first encrypted code with the second encrypted code.

18. The system of claim 14, wherein:

the method further includes obtaining, by the motion enable unit, a first code, the generating, by the motion enable unit, processed information by processing information using a first secret comprises generating an encrypted code by encrypting the first code using the first secret, and the verifying, by the safety control unit, the closed state of the switch-comprises obtaining a second code, generating a decrypted code by decrypting the encrypted code using the second secret, and comparing the decrypted code with the second code, wherein the first code and the second code have a same value.

19. A non-transitory computer readable medium comprising executable instructions, the executable instructions being executed by a remote control device and a safety control device communicating with each other via a wireless connection, wherein the remote control device is configured to remotely control a radiotherapy (RT) device and comprises a switch, a motion enable unit, and a hand control unit, the switch being configured to control a connection between the motion enable unit and the hand control unit, the safety control device comprises a communication unit and a safety control unit, the communication unit including a wireless transmitter, and when the executable instructions are executed by the remote control device and the safety control device, direct the remote control device and the safety control device to perform a method, the method comprising:

generating, by the motion enable unit, processed information by processing information using a first secret;

acquiring, by the hand control unit, the processed information from the motion enable device only when the switch is in a closed state;

transmitting, by the hand control unit, the processed information to the safety control device via the wireless connection;

receiving, by the communication unit, the processed information via the wireless connection;

verifying, by the safety control unit, the closed state of the switch by processing the processed information using a second secret that matches the first secret; and enabling control of the RT device when the closed state of the switch is verified, wherein the motion enable unit and the safety control unit are hardware circuits without software, the switch is a physical key on the motion enable unit, the hand control unit is a component with software, the first secret and the second secret are respectively stored in the hardware circuits of the motion enable unit and the safety control unit, not known to any components with software, and the first secret and the second secret having been paired with each other during an initial set-up of the system, the processed information is accessible to the software of the hand control unit only when the switch is in the closed state, and an opening of the switch causes the hand control unit to be physically disconnected from the hardware circuit of the motion enable unit and accordingly causes unavailability of the processed information to the software of the hand control unit.

* * * * *